United States Patent [19]

Clough et al.

[11] Patent Number: 4,636,247

[45] Date of Patent: Jan. 13, 1987

[54] HETEROCYCLIC COMPOUNDS

[75] Inventors: John M. Clough, Buckinghamshire; Timothy Lewis, Berkshire; Michael B. Gravestock, Cheshire, all of England

[73] Assignee: Imperial Chemical Industries PLC, London, England

[21] Appl. No.: 578,033

[22] Filed: Feb. 8, 1984

[30] Foreign Application Priority Data

Mar. 9, 1983 [GB] United Kingdom ................ 8306512

[51] Int. Cl.$^4$ .................... C07D 405/06; A01N 43/00; A01N 43/653

[52] U.S. Cl. ............................................. 71/92; 71/76; 71/77; 71/DIG. 1; 548/262; 548/101; 548/336; 514/184; 514/383; 514/397

[58] Field of Search ....................... 548/101, 262, 336; 424/245, 269, 273 R; 71/76, 92; 514/184, 383, 397

[56] References Cited

U.S. PATENT DOCUMENTS 4,289,526  9/1981  Worthington et al. .............. 548/262
4,351,839  9/1982  Chan ..................... 548/262

FOREIGN PATENT DOCUMENTS 0089100  9/1983  European Pat. Off. ............ 548/262
0097469  1/1984  European Pat. Off. ............ 548/262
2095236A  9/1982  United Kingdom ................ 548/262

Primary Examiner—Glennon H. Hollrah
Assistant Examiner—D. Dinner
Attorney, Agent, or Firm—Cushman, Darby & Cushman

[57] ABSTRACT

Triazoles and imidazoles of the formula (I):

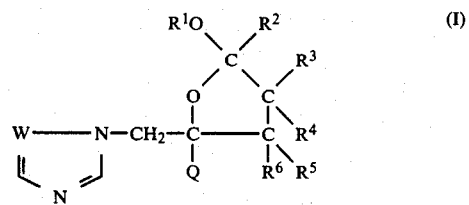

and stereoisomers thereof, wherein W is CH or N; Q is optionally substituted aryl (especially optionally substituted phenyl), optionally substituted aralkyl, or alkyl; $R^1$ is H, alkyl, cycloalkyl, alkenyl, alkynyl, acyl, optionally substituted aralkyl, optionally substituted phenyl, or is an alkyl or aralkyl group substituted with an ether, hydroxyl, carboxylic ester, or ketone group; $R^2$, $R^3$, $R^4$, $R^5$ and $R^6$, which may be the same or different, are H, alkyl, cycloalkyl, optionally substituted aralkyl, or optionally substituted phenyl; and acid salts and metal complexes thereof. These compounds are useful as plant growth regulators and fungicides. Other values for $R^1$ include $C_1$-$C_4$ alkoxycarbonyl, $C_1$-$C_4$ alkoxyalkyl and phenyl or benzyl substituted by benzyl.

7 Claims, No Drawings

HETEROCYCLIC COMPOUNDS

This invention relates to triazole and imidazole compounds useful as plant growth regulators and fungicides, to processes for preparing them, to plant growth regulatory and fungicidal compositions containing them, and to methods of using them to regulate plant growth and to combat fungi, especially fungal infections in plants.

The invention provides a compound having the general formula (I):

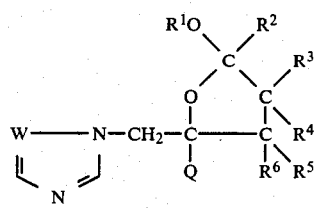

and stereoisomers thereof, wherein W is CH or N; Q is optionally substituted aryl (especially optionally substituted phenyl), optionally substituted aralkyl, or alkyl; $R^1$ is H, alkyl, cycloalkyl, alkenyl, alkynyl, acyl, optionally substituted aralkyl, optionally substituted phenyl, or is an alkyl or aralkyl group substituted with an ether, hydroxyl, carboxylic ester, or ketone group; $R^2$, $R^3$, $R^4$, $R^5$ and $R^6$, which may be the same or different, are H, alkyl, cycloalkyl, optionally substituted aralkyl, or optionally substituted phenyl; and acid salts and metal complexes thereof.

Preferred alkyl groups contain from 1 to 6, especially 1 to 4, carbon atoms. Preferred cycloalkyl groups are cyclopropyl, cyclobutyl, cyclopentyl and cyclohexyl groups. The alkyl moiety in aralkyl groups preferably contains from 1 to 4 carbon atoms.

The compounds of the invention contain at least 2 chiral centres; consequently, each compound has at least 4 stereoisomeric forms, and these can be separated into individual isomers by methods known in the art, and this invention embraces such isomers.

Examples of suitable substituent groups for Q, $R^1$, $R^2$, $R^3$, $R^4$, $R^5$ and $R^6$ when they represent aralkyl or aryl, especially benzyl or phenyl, are halogen, haloalkyl, alkyl, alkoxy (especially containing 1 to 4 carbon atoms), optionally substituted phenyl and optionally substituted phenoxy. Phenyl is preferred to benzyl. Other values for $R^1$ include $C_1$-$C_4$ alkoxycarbonyl, $C_1$-$C_4$ alkoxyalkyl and phenyl or benzyl substituted by benzyl.

Suitably the aryl, especially phenyl, is unsubstituted or substituted with 1, 2, or 3 ring substituents, which may be the same or different, as defined above. Examples of Q, $R^1$, $R^2$, $R^3$, $R^4$, $R^5$ and $R^6$ are phenyl, 2-, 3- or 4-chlorophenyl, 2,4- or 2,6-dichlorophenyl, 2,4- or 2,6-difluorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxyphenyl, 2-fluoro-4-chlorophenyl, 2-chloro-4-fluorophenyl, 2-, 3- or 4-methylphenyl, 2-, 3- or 4-ethylphenyl, 2-, 3- or 4-trifluoromethylphenyl, 4-phenylphenyl (4-biphenylyl), 2-chloro-4-methoxyphenyl, 2-fluoro-4-methoxyphenyl, 2-chloro-4-methylphenyl, 2-fluoro-4-methylphenyl, 4-isopropylphenyl, 2-methyl-4-chlorophenyl or 2-methyl-4-fluorophenyl.

When Q, $R^1$, $R^2$, $R^3$, $R^4$, $R^5$ or $R^6$ is alkyl it can be a straight or branched chain alkyl group having 1 to 6, e.g. 1 to 4, carbon atoms; examples are methyl, ethyl, propyl (n- or iso-propyl) and butyl (n-, sec-, iso- or t-butyl). When Q is alkyl, it is preferably t-butyl.

The moiety W is preferably =N—, i.e., the preferred compounds are triazoles.

The salts can be salts with inorganic or organic acids e.g., hydrochloric, nitric, sulphuric, acetic, 4-toluenesulphonic or oxalic acid.

Suitably the metal complex is one including, as the metal, copper, zinc, manganese or iron. It preferably has the formula:

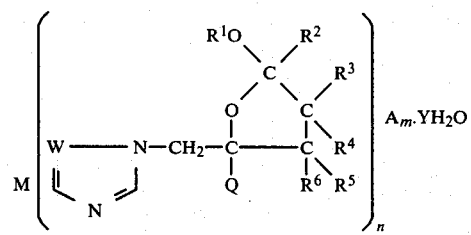

wherein W, Q, $R^1$, $R^2$, $R^3$, $R^4$, $R^5$ and $R^6$ are as defined above, M is a metal, A is an anion (e.g., a chloride, bromide, iodide, nitrate, sulphate, or phosphate anion), n is 2 or 4, y is 0 or an integer of 1 to 12, and m is an integer consistent with valency.

Examples of the compounds of the invention are shown in Table I. $R^3$, $R^4$, $R^5$ and $R^6$ are hydrogen atoms in each example, and W is an N-atom, i.e. the compounds conform to the general formula:

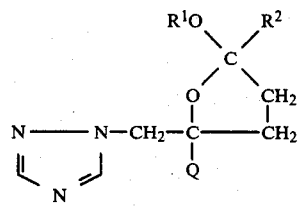

TABLE I

| Compound No | Q | $R^1$ | $R^2$ | Diastereomer* | Melting point (°C.) |
|---|---|---|---|---|---|
| 1 | 2,4-di-Cl—$C_6H_3$ | H | H | 4:3 | 171–174 |
| 2 | 2,4-di-Cl—$C_6H_3$ | $CH_3$ | H | A | 111–112 |
| 3 | 2,4-di-Cl—$C_6H_3$ | $CH_3$ | H | B | 133–134 |
| 4 | 2,4-di-Cl—$C_6H_3$ | $CH_3$ | H | 2:1 | 95–123 |
| 5 | 2,4-di-Cl—$C_6H_3$ | $CH_3$ | H | 1:2 | 95–105 |
| 6 | 2,4-di-Cl—$C_6H_3$ | $C_2H_5$ | H | A | Gum |
| 7 | 2,4-di-Cl—$C_6H_3$ | $C_2H_5$ | H | B | 156–157 |
| 8 | 2,4-di-Cl—$C_6H_3$ | $C(CH_3)_3$ | H | A | 118–119.5 |
| 9 | 2,4-di-Cl—$C_6H_3$ | $C(CH_3)_3$ | H | B | 97–99 |
| 10 | 2,4-di-Cl—$C_6H_3$ | $CH_2C≡CH$ | H | A | Oil |
| 11 | 2,4-di-Cl—$C_6H_3$ | $CH_2C≡CH$ | H | B | 132–135 |

TABLE I-continued

| Compound No | Q | $R^1$ | $R^2$ | Diastereomer* | Melting point (°C.) |
|---|---|---|---|---|---|
| 12 | 2,4-di-Cl—$C_6H_3$ | $COCH_3$ | H | 3:2 | 141–148 |
| 13 | 2,4-di-Cl—$C_6H_3$ | $CO(CH_3)_3$ | H | A | 114–116 |
| 14 | 2,4-di-Cl—$C_6H_3$ | $CO(CH_3)_3$ | H | B | 129–131 |
| 15 | 2,4-di-Cl—$C_6H_3$ | $CO(CH_2)_6CH_3$ | H | A | 88–91 |
| 17 | 2,4-di-Cl—$C_6H_3$ | $CH_2CO_2C_2H_5$ | H | A | 103–104 |
| 18 | 2,4-di-Cl—$C_6H_3$ | $CH_2CO_2C_2H_5$ | H | B | 114–117 |
| 19 | 2,4-di-Cl—$C_6H_3$ | $CH_2CH_2OCH_2CH_2:CH_2$ | H | 1 diastereomer | Oil |
| 20 | 2,4-di-Cl—$C_6H_3$ | $CH_2CH_2OCH_2(2,4$-di-Cl—$C_6H_3)$ | H | 1 diastereomer | 111–114 |
| 21 | 2,4-di-Cl—$C_6H_3$ | $CO(4$-$NO_2$—$C_6H_4)$ | H | A | 181–183 |
| 22 | 2,4-di-Cl—$C_6H_3$ | $CO(4$-$NO_2$—$C_6H_4)$ | H | B | Oil |
| 23 | 2,4-di-Cl—$C_6H_3$ | $CH_2CH_2OH$ | H | A | 126–128 |
| 24 | 2,4-di-Cl—$C_6H_3$ | $CH_2CH_2OH$ | H | B | 162–165 |
| 25 | 4-Cl—$C_6H_4$ | $CH_2CH_2OH$ | H | 1 diastereomer | 102–103 |
| 26 | 2,4-di-Cl—$C_6H_3$ | $CH_3CH_2CH_2$ | H | A | 73–75 |
| 27 | 2,4-di-Cl—$C_6H_3$ | $CH_3CH_2CH_2$ | H | B | 112–114 |
| 28 | 2,4-di-Cl—$C_6H_3$ | $(CH_3)_2CH$ | H | A | 89–90 |
| 29 | 2,4-di-Cl—$C_6H_3$ | $(CH_3)_2CH$ | H | B | 148–149 |
| 30 | 2,4-di-Cl—$C_6H_3$ | H | $CH_3$ | 3:2 | 155–160 |
| 31 | 2,4-di-Cl—$C_6H_3$ | $CH_3$ | $CH_3$ | 2:1 | 126–151 |
| 32 | 2,4-di-Cl—$C_6H_3$ | $CH_3CH_2$ | $CH_3$ | A | 99–101 |
| 33 | 2,4-di-Cl—$C_6H_3$ | $CH_3CH_2$ | $CH_3$ | B | 158–160 |
| 34 | 2,4-di-Cl—$C_6H_3$ | $CH_3CH_2CH_2$ | $CH_3$ | A | Oil |
| 35 | 2,4-di-Cl—$C_6H_3$ | $CH_3CH_2CH_2$ | $CH_3$ | B | 114–115 |
| 36 | 2,4-di-Cl—$C_6H_3$ | H | $CH_3CH_2$ | 2:1 | 137–150 |
| 37 | 2,4-di-Cl—$C_6H_3$ | $CH_3$ | $CH_3CH_2$ | A | 144.5–145.5 |
| 38 | 2,4-di-Cl—$C_6H_3$ | $CH_3$ | $CH_3CH_2$ | B | 106–107 |
| 39 | 2,4-di-Cl—$C_6H_3$ | $CH_3CH_2$ | $CH_3CH_2$ | A | 97–98 |
| 40 | 2,4-di-Cl—$C_6H_3$ | $CH_3CH_2$ | $CH_3CH_2$ | B | 139–140 |

*Diastereomer A is the less polar isomer.
Diastereomer B is the more polar isomer.
Where a ratio of diastereomers is given, the compound is a mixture of diastereomers A and B, not necessarily respectively.

The compounds of the invention of general formula (I):

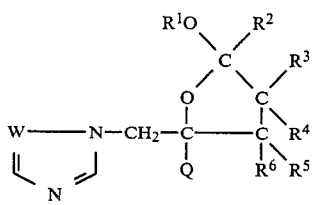

wherein Q, W, $R_1$, $R^2$, $R^3$, $R^4$, $R^5$ and $R^6$ are as defined above but $R^1$ is not a hydrogen atom can be prepared from the analogous compounds in which $R^1$ is a hydrogen atom either (a) by acetalisation under acidic conditions with an alcohol of general formula $R^1OH$, wherein $R^1$ is as defined above, either in a suitable solvent or with an excess of the alcohol itself forming the solvent, or (b) by successive treatment in a suitable solvent with a strong base (for example, sodium hydride) and a compound of general formula $R^1X$, wherein $R^1$ is as defined above and X is a leaving group (for example, a halogen or a tosyloxy group).

Compounds of general formula (I) wherein $R^1$ is a hydrogen atom can be prepared by hydrolysis under acidic conditions of either (a) compounds of general formula (I) wherein $R^1$ is not a hydrogen atom or (b) alcohols of general formula (II):

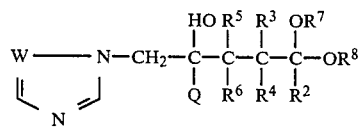

wherein Q, W, $R^1$, $R^2$, $R^3$, $R^4$, $R^5$ and $R^6$ are as defined above, and $R^7$ and $R^8$, which may be the same or different, are alkyl or alkenyl groups or together form a ring (for example, a 1,3-dioxolane or 1,3-dioxane ring).

Alcohols of general formula (II) can be prepared by treating either epoxides of general formula (III):

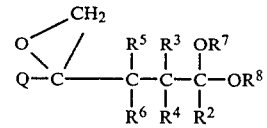

wherein Q, $R^2$, $R^3$, $R^4$, $R^5$, $R^6$, $R^7$ and $R^8$ are as defined above, or halohydrins of general formula (IV):

$$\begin{array}{c} OH \quad R^5 \quad R^3 \quad OR^7 \\ | \quad \quad | \quad \quad | \quad \quad | \\ Q-C-\!\!-\!\!-C-C-C-OR^8 \\ | \quad \quad | \quad \quad | \quad \quad | \\ CH_2 \quad R^6 \quad R^4 \quad R^2 \\ | \\ A \end{array} \quad (IV)$$

wherein Q, $R^2$, $R^3$, $R^4$, $R^5$, $R^6$, $R^7$ and $R^8$ are as defined above and A is a halogen atom (a chlorine, bromine, or iodine atom), either with 1,2,4-triazole or with imidazole, each in the presence of an acid-binding agent or in the form of one of its alkali metal salts, in a convenient solvent (such as dimethylformamide or acetonitrile) and at a convenient temperature.

Epoxides of general formula (III), or halohydrins of general formula (IV), or mixtures of them both, are formed when halo-ketones of general formula (V):

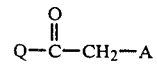

wherein Q and A are as defined above, are treated with Grignard reagents of general formula (VI):

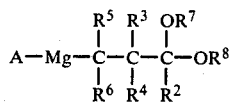

(VI)

wherein A, $R^2$, $R^3$, $R^4$, $R^5$, $R^6$, $R^7$ and $R^8$ are as defined above.

Halo-ketones of general formula (V) can be prepared by standard methods described in the chemical literature.

Grignard reagents of general formula (VI) can be prepared from the corresponding halides by methods described in the chemical literature. The following references provide examples of methods for preparing such halides and the Grignard reagents from them:

G Büchi and H Wüest, *J. Org. Chem.*, 1969, 34, 1122;
D. C. Kriesel and O. Gisvold, *J. Pharm. Sci.*, 1971, 60, 1250;
J. C. Stowell, *J. Org. Chem.*, 1976, 41, 560;
T. Sato, T. Kawara, K. Sakata and T. Fujisawa, *Bull. Chem. Soc. Japan*, 1981, 54, 505.

In some cases, treatment of halo-ketones of general formula (V) with Grignard reagents of general formula (VI) leads directly to halides of general formula (VII):

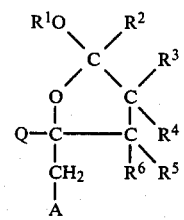

(VII)

wherein Q, A, $R^2$, $R^3$, $R^4$, $R^5$ and $R^6$ are as defined above, and either $R^1 = R^7$ or, if $R^7$ and $R^8$ together formed a ring in the original Grignard reagent, $R^1 = -(CH_2)_n OH$ where n is an integer.

Halides of general formula (VII) can be converted into compounds of general formula (I) by treatment either with 1,2,4-triazole or with imidazole, each in the presence of an acid-binding agent or in the form of one of its alkali metal salts, in a convenient solvent (such as dimethylformamide or acetonitrile) and at a convenient temperature.

Similarly, in some cases, treatment of epoxides of general formula (III) with 1,2,4-triazole or with imidazole can lead directly to compounds of general formula (I) in which either $R^1 = R^7$ or, if $R^7$ and $R^8$ together formed a ring in the epoxide (III), $R^1 = -(CH_2)_n OH$ where n is an integer.

Epoxides of general formula (III) can also be obtained by treatment of ketones of general formula (VIII):

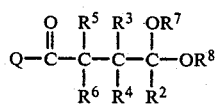

(VIII)

wherein Q, $R^2$, $R^3$, $R^4$, $R^5$, $R^6$, $R^7$ and $R^8$ are as defined above, with either dimethylsulphonium methylide or dimethyloxoxsulphonium methylide (E. J. Corey and M. Chaykovsky, J. Amer. Chem. Soc, 1962, 84, 3782 and 1965, 87, 1353 respectively).

Alternatively, epoxides of general formula (III) can be prepared by oxidation of olefins of general formula (IX):

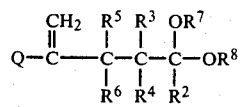

(IX)

wherein Q, $R^2$, $R^3$, $R^4$, $R^5$, $R^6$, $R^7$ and $R^8$ are as defined above, using standard methods described in the chemical literature.

In an alternative approach, halides of general formula (VII) can be prepared by treatment of olefins of general formula (X):

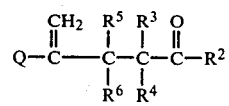

(X)

wherein Q, $R^2$, $R^3$, $R^4$, $R^5$ and $R^6$ are as defined above, with a halogen (such as bromine or iodine), a base (such as pyridine) and an alcohol of general formula $R^1 OH$, wherein $R^1$ is as defined above, either in a suitable solvent, or with an excess of the alcohol forming the solvent.

Ketones of general formula (VIII) and olefins of general formulae (IX) and (X) can be prepared by methods which have been described previously.

In an alternative approach, compounds of the general formula (I) wherein $R^1$ is a hydrogen atom can be prepared by treating epoxides of general formula (XI):

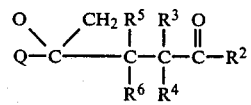

(XI)

wherein Q, $R^2$, $R^3$, $R^4$, $R^5$ and $R^6$ are as defined above, either with 1,2,4-triazole or with imidazole, each in the presence of an acid-binding agent or in the form of one of its alkali metal salts, in a convenient solvent (such as dimethylformamide or acetonitrile) and at a convenient temperature.

Epoxides of general formula (XI) can be prepared from olefins of general formula (X) by treatment with an appropriate oxidising agent (a peracid, for example) by methods described in the chemical literature.

The salts and metal complexes of the compounds of general formula (I) can be prepared from the latter by known methods. For example, the complexes can be made by reacting the uncomplexed compound with a metal salt in a suitable solvent.

The compounds, salts and metal complexes are active fungicides, particularly against the diseases:
*Piricularia oryzae* on rice
*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants
*Plasmopara viticola* on vines
*Erysiphe graminis* (powdery mildew) on barley and wheat and other powdery mildews on various hosts such as
*Sphaerotheca fuliginea* on cucurbits (e.g. cucumber),

*Podosphaera leucotricha* on apples and *Uncinula necator* on vines

*Helminthosporium* spp. and *Rhynchosporium* spp. on cereals

*Cercospora arachidicola* on peanuts and other *Cercospora* species on for example sugar beet, bananas and soya beans

*Botrytis cinerea* (grey mould) on tomatoes, strawberries, vines and other hosts

*Phytophthora infestans* (late blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and italicum on oranges and *Gloeosporium musarum* on bananas). Further some of the compounds are active as seed dressings against: Fusarium spp., Septoria spp., Tilletia spp. (ie. bunt, a seed borne disease of wheat), Ustilago spp., Helminthosporium spp. on cereals, *Rhizoctonia solani* on cotton and *Corticium sasakii* on rice. The compounds can move acropetally in the plant tissue. Moreover, the compounds can be volatile enough to be active in the vapour phase against fungi on the plant. They also have plant growth regulating activity.

The compounds are also useful for the treatment of candidiasis and human dermatophyte infections.

The compounds may be used as such for fungicidal purposes but are more conveniently formulated into compositions for such usage.

The invention thus further provides a fungicidal composition comprising a compound of general formula (I) as hereinbefore defined, or a salt or metal complex, thereof; and, optionally, a carrier or diluent.

The invention also provides a method of combating fungi, which comprises applying to a plant, to seed of a plant or to the locus of a plant or seed, a compound, or a salt, metal complex thereof, as hereinbefore defined, or a composition containing the same.

The invention also provides a method of regulating the growth of plants, which comprises applying to the plant, to seed of the plant, or to the locus of the plant or seed, a compound, or a salt or metal complex thereof as hereinbefore defined, or a composition containing the same.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied.

The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and perenne, *Agrostis tenuis, Cynodon dactylon* (Bermuda grass), *Dactylis glomerata*, Festuca spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape or reduce the need for pruning, of fruit trees (e.g. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides a fungicidal or plant growth regulating composition comprising a compound of general formula (I) as hereinbefore defined, or a salt or metal complex thereof; and, optionally, a carrier or diluent.

The invention also provides a method of combating fungi, which comprises applying to a plant, to seed of a plant, or to the locus of the plant or seed, a compound, or salt or metal complex thereof as hereinbefore defined; or a composition containing the same.

The invention also provides a method of regulating plant growth, which comprises applying to the plant, to seed of a plant or to the locus of a plant or seed, a compound, or a salt or metal complex thereof, as hereinbefore defined, or a composition combining the same.

The compounds, salts, and metal complexes, can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g., fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g., alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also other compound(s) having biological activity, e.g., compounds having similar or complementary fungicidal or plant growth activity or compounds having plant growth regulating, herbicidal or insecticidal activity.

The other fungicidal compound can be, for example, one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides.

Examples of suitable plant growth regulating compounds, which can display synergy in admixture, or use, with the invention compounds are the gibberellins (e.g., $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat*, benzoylprop-ethyl 3,6-dichloropicolinic acid, and tecnazene. Synergy will be most likely to occur with those of the foregoing which are quaternary ammonium compounds and with those marked with an asterisk.

The use of the compounds of general formula (I) in conjunction with gibberellins can be useful where it is desired to reduce the plant growth regulating effects of the compounds (e.g. where they are to be used as fungicides). Where the compounds are being applied to the soil surrounding the plants or to the roots of the plant, the plant growth regulating effects of the compounds may possibly be reduced by using also certain types of phenoxybenzoic acids and their derivatives.

The following Examples illustrate the invention.

EXAMPLE 1

This example illustrates the preparation of 2-(2,4-dichlorophenyl)-2-(1,2,4-triazol-1-yl)methyl-5-hydroxytetrahydrofuran (compound number 1 of Table I) and 2-(2,4-dichlorophenyl)-2-(1,2,4-triazol-1-yl)methyl-5-(2-hydroxyethoxy)tetrahydrofuran (compound number 23 of Table I).

A solution of 2,2',4'-trichloroacetophenone (11.2 g) in dry tetrahydrofuran (THF: 25 ml) was added dropwise over 0.5 hours to a solution of the Grignard reagent from 2-(2-bromoethyl)-1,3-dioxolane (10.8 g) and magnesium (1.44 g) (see G Büchi and H Wüest, J. Org. Chem., 1969, 34, 1122) in THF (70 ml), cooled in an ice bath. The mixture was stirred at room temperature overnight and was then poured into 5% aqueous ammonium chloride and extracted with ether. The extracts were washed with water and brine, then dried over sodium sulphate and concentrated under reduced pressure. The resulting red oil was added to a solution of sodium 1,2,4-triazole (6.0 g) in dimethylformamide (25 ml) and the mixture was heated at 80° C. for 5 hours then allowed to cool, poured into water and extracted with ethyl acetate. The extracts were washed with water, dried over sodium sulphate, and concentrated under reduced pressure to give a red oil (12.8 g). Chromatography on a column of silica gel gave 1-(1,2,4-triazol-1-yl)-2-(2,4-dichlorophenyl)-4-(1,3-dioxolan-2-yl)butan-2-ol (6.50 g, 36% yield from the trichloroacetophenone) as a solid. An analytical sample, recrystallised from ether/petrol, had melting point 92°–94° C. (Found: C,50.5; H,5.0; N,11.3%. C$_{15}$H$_{17}$Cl$_2$N$_3$O$_3$ requires C,50.42; H,4.76; N,11.76%).

In a second experiment, using essentially the same procedure, the major product was a single diastereomer (A) of 2-(2,4-dichlorophenyl)-2-(1,2,4-triazol-1-yl)methyl-5-(2-hydroxyethoxy)tetrahydrofuran (40% yield from the trichloroacetopohenone), melting point 126°–128° C., $^1$H n.m.r CDCl$_3$): δ4.75 (1H,d,OCHO), 4.86 (2H,q,CH$_2$N). (Found: C,50.3; H,4.8; N,11.5%. C$_{15}$H$_{17}$Cl$_2$N$_3$O$_3$ requires as above).

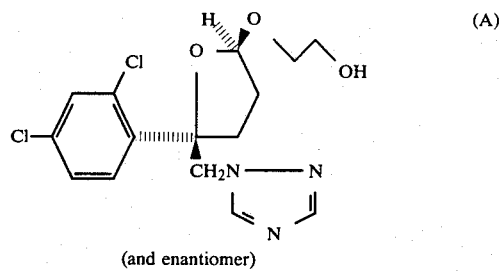

(and enantiomer)

A mixture of 2-(2,4-dichlorophenyl)-2-(1,2,4-triazol-1-yl)methyl-5-(2-hydroxyethoxy)tetrahydrofuran (15.0 g), 4M hydrochloric acid (100 ml) and tetrahydrofuran (45 ml) was refluxed for 0.5 hours, allowed to cool, poured onto solid sodium bicarbonate, and extracted with ethyl acetate. The extracts were washed with water, dried over sodium sulphate and concentrated to give a 4:3 mixture of diastereomers of 2-(2,4-dichlorophenyl)-2-(1,2,4-triazol-1-yl)methyl-5-hydroxytetrahydrofuran (11.9 g, 90%) as a white solid, melting point 171°–174° C. (Found: C,49.8; H,4.3; N,13.1%. C$_{13}$H$_{13}$Cl$_2$N$_3$O$_3$ requires: C,49.7; H,4.1; N,13.4%).

The isomeric species 1-(1,2,4-triazol-1-yl)-2-(2,4-dichlorophenyl)-4-(1,3-dioxolan-2-yl)butan-2-ol could be hydrolysed to give the same product in exactly the same way.

EXAMPLE 2

This example illustrates the preparation of 2-(2,4-dichlorophenyl)-2-(1,2,4-triazol-1-yl)methyl-5-ethoxycarbonylmethoxytetrahydrofuran (compounds numbers 17 and 18 of Table I).

2-(2,4-Dichlorophenyl)-2-(1,2,4-triazol-1-yl)methyl-5-hydroxytetrahydrofuran (3.14 g, prepared as described in Example 1) was added in portions at room temperature to a stirred suspension of sodium hydride (0.30 g) in tetrahydrofuran (31.5 ml) and dimethylformamide (3.5 ml). When evolution of hydrogen ceased, ethyl bromoacetate (1.8 g) was added dropwise (mild exotherm) and the reaction mixture was stirred for 2 hours, then poured into dilute hydrochloric acid and extracted with ethyl acetate. The extracts were washed with water, dried over sodium sulphate and concentrated under reduced pressure to give an orange oil (3.5 g) which was purified by chromatography on silica gel using petrol/ethyl acetate 1:1 as eluant to give:

(i) Diastereomer A of the title compound (1.5 g,38%) as a white solid, eluted first. An analytical sample, recrystallised from ethyl acetate/petrol had melting point 103°–104° C., $^1$H n.m.r. (CDCl$_3$): δ4.88(2H,q,CH$_2$N), 5.39(1H,d,OCHO).

(ii) Diastereomer B of the title compound (0.6 g,15%) as a white solid, eluted second. An analytical sample, recrystallised from ethyl acetate/petrol, had melting point 114°–117° C., $^1$H n.m.r. (CDCl$_3$): δ4.45(2H,q,CH$_2$N), 5.25(1H,d,OCHO).

Nuclear Overhauser effect experiments using proton n.m.r. spectroscopy at 400 MHz enabled the following stereochemistry to be assigned to diastereomer A:

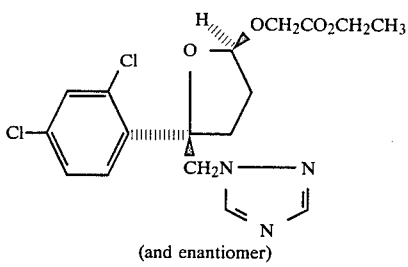

(and enantiomer)

EXAMPLE 3

This example illustrates a preparation of 2-(2,4-dichlorophenyl)-2-(1,2,4-triazol-1-yl)methyl-5-methoxytetrahydrofuran (compounds numbers 2, 3, 4 and 5 of Table I).

A solution of bromine (1.4 g) in dry methanol (10 ml) was added dropwise to a stirred mixture of 4-(2,4-dichlorophenyl)pent-4-enal (2.0 g ), (prepared as described in UK patent application No. GB 2115408A, 5.1.1983, and pyridine (0.7 g) in dry methanol (40 ml) at 0° C. (bromine decolourised). Following the addition, the mixture was stirred at room temperature for 0.5 hours, then diluted with ether and washed successively with water, dilute hydrochloric acid, and saturated brine. The resulting solution was dried over magnesium sulphate and concentrated under reduced pressure to give a yellow oil (3.2 g) containing a mixture of diastereomers of 2-bromomethyl-2-(2,4-dichlorophenyl)-5-methoxytetrahydrofuran.

Part of this crude product was added to a solution of sodium triazole [from 1,2,4-triazole (1.38 g) and sodium hydride (0.75 g)] in dimethylformamide (50 ml) and the mixture was heated at 160° C. (external temperature) for 4 hours, then allowed to cool. The mixture was diluted with water and extracted with ether. The extracts were washed with water, dried over magnesium sulphate and concentrated under reduced pressure to give a yellow oil (2.34 g). Chromatography on silica gel using ether as eluant gave a mixture of diastereomers of the title compound [550 mg, 20% yield from 4-(2,4-dichlorophenyl)-pent-4-enal]. Crystallisation from diethyl ether gave:

(i) 300 mg of a white solid, a 2:1 mixture of diastereomers of the title compound, partially melting at 95°–96° C. and fully melting at 122°–123° C. (Found: C,51.02; H,4.54; N,13.07%. $C_{14}H_{15}Cl_2N_3O_2$ requires C,51.22; H,4.57; N,12.80%).

(ii) 250 mg of an almost white solid (concentrated mother liquors), a 1:2 mixture of diastereomers of the title compound, melting point 95°–105° C.

Careful chromatography in diethyl ether of a second batch of the mixed diasteromers, followed by crystallisation from dichloromethane/40°–60° petrol, gave the pure diastereomers as colourless crystalline compounds:

Diastereomer A: m.p. 111°–112° C., $R_f$(EtOAc) 0.31, $^1H$ n.m.r. (CDCl$_3$): δ 3.53 (3H,s), 4.63 and 5.13 (each 1H,d J 16 Hz), 5.2 (1H,m).

Diastereomer B: m.p. 133°–134° C., $R_f$(EtOAc) 0.28, $^1H$ n.m.r. (CDCl$_3$): δ 3.40 (3H,s), 4.30 and 4.71 (each 1H, d J 14 Hz), 5.02 (1H, d J 5 Hz).

EXAMPLE 4

This example illustrates the preparation of 2-(2,4-dichlorophenyl)-2-(1,2,4-triazol-1-yl)methyl-5-methoxy-5-methyltetrahydrofuran (compound no. 31 of Table I).

A solution of 4-(2,4-dichlorophenyl)pent-4-enal (26.0 g) in dry diethyl ether was added dropwise to a stirred solution of methylmagnesium iodide [from magnesium (4.09 g) and methyl iodide (24.14 g)] in diethyl ether (total volume of diethyl ether ca. 200 ml). Following the addition, the reaction mixture was stirred at room temperature for 1 hour then poured into a mixture of ice and dilute hydrochloric acid, and extracted with ether. The extracts were washed with water, dried over magnesium sulphate, concentrated under reduced pressure, and chromatographed on a column of silica gel (eluting with dichloromethane: 60°–80° petrol, 1:1) to give 2-(2,4-dichlorophenyl)hexan-5-ol (19.2 g, 69%) as an almost colourless oil.

A mixture of pyridinium dichromate (49 g) and 2-(2,4-dichlorophenyl)hexan-5-ol (16 g) in dry dimethylformamide (100 ml) was stirred overnight at room temperature then poured into water and extracted with ether. The extracts were washed successively with dilute hydrochloric acid and water, then dried over magnesium sulphate and concentrated under reduced pressure to give almost pure 2-(2,4-dichlorophenyl)hex-1-en-5-one (14.5 g, 91%) as a yellow oil, $^1H$ n.m.r. (CDCl$_3$): δ2.18 (3H,s), 2.4–3.0 (4H,m), 5.15 (1H,s), 5.41 (1H,s), 7.2–7.6 (3H, m).

By the 2 step method described in Example 3 for the conversion of 4-(2,4-dichlorophenyl)pent-4-enal into 2-(2,4-dichlorophenyl)-2-(1,2,4-triazol-1-yl)methyl-5-methoxytetrahydrofuran, 2-(2,4-dichlorophenyl)hex-1-en-5-one was converted into the title compound (52% over both steps), a white solid, m.p. 126°–151° C., a 2:1 mixture of diastereomers. Selected proton n.m.r. data (CDCl$_3$): Major diastereomer: δ1.57 (s, C—CH$_3$), 3.44 (s,OCH$_3$). Minor diastereomer: δ1.42 (s,C—CH$_3$), 3.20 (s,OCH$_3$).

EXAMPLE 5

This Example illustrates the preparation of 2-(2,4-dichlorophenyl)-2-(1,2,4-triazol-1-yl)methyl-5-hydroxy-5-methyltetrahydrofuran (compound no. 30 of Table I).

A solution of 2-(2,4-dichlorophenyl)hex-1-en-5-one (0.50 g, prepared as described in Example 4) in dry dichloromethane (15 ml) was cooled to 0° C. and 3-chloroperbenzoic acid (0.38 g) was added. The mixture was stirred at 0° C. for 1 hour and then at room temperature for a further 4 hours. It was then diluted with ether, washed successively with aqueous sodium hydroxide and water, dried over magnesium sulphate, and concentrated under reduced pressure to give a pale yellow oil (0.44 g) consisting mainly of 2-(2,4-dichlorophenyl)-1,2-epoxyhexan-5-one, $^1H$ n.m.r. (CDCl$_3$): δ 2.11 (3H,s), 2.79 and 3.06 (each 1H, d J 6 H2). A second experiment using the same procedure gave a further sample of the crude epoxide (1.58 g from 1.5 g of olefin) which was combined with the first batch.

The crude epoxide (1.90 g) was added to a solution of sodium triazole [from 1,2,4-triazole (1.24 g) and sodium hydride (0.43 g)] in dry dimethylformamide (50 ml). The resulting mixture was heated at 90° C. for 2 hours then allowed to cool, poured into water and extracted with ethyl acetate. The extracts were washed with water, dried over magnesium sulphate, and concentrated under reduced pressure to give a yellow solid (1.8 g). Trituration with diethyl ether left a white solid [1.06 g, 42% from 2-(2,4-dichlorophenyl)hex-1-en-5-one], m.p.

155°–160° C., a 3:2 mixture of diastereomers of the title compound, $^1$H n.m.r. (CDCl$_3$): δ 1.44 s, CH$_3$ of major diastereomer; δ 1.55 s, CH$_3$ of minor diastereomer. The infrared spectrum (nujol mull: 3200 cm$^{-1}$ but no C=O absorption) confirmed that the solid product is in the form of the cyclic hemiketal.

EXAMPLE 6

This example illustrates the preparation of 2-(2,4-dichlorophenyl)-2-(1,2,4-triazol-1-yl)methyl-5-propoxy-5-methyltetrahydrofuran (compound nos. 34 and 35 of Table I).

A solution of 2-(2,4-dichlorophenyl)-2-(1,2,4-triazol-1-yl)methyl-5-hydroxy-5-methyltetrahydrofuran (1.0 g) in dry propan-1-ol (50 ml) containing concentrated sulphuric acid (3 ml) was stirred at room temperature for 8 hours then heated at 90° C. for 8 hours and allowed to cool. Solid sodium bicarbonate and then water were added and the mixture was extracted with ether. The extracts were washed with water, dried over magnesium sulphate and concentrated under reduced pressure to give a yellow oil. Chromatography on silica gel using diethyl ether as eluant gave the title compound:

(i) Diastereomer A (0.20 g, 18%) as a yellow oil, $^1$H n.m.r. (CDCl$_3$): δ 1.58 (3H,s), 4.46 and 5.24 (each 1 H, d J 16 Hz).

(ii) Diastereomer B (0.60 g, 53%) as a white solid, with m.p. 114°–115° C. following trituration with petrol, $^1$H n.m.r. (CDCl$_3$): δ 1.43 (3H,s), 4.26 and 4.68 (each 1H, d J 16 Hz).

EXAMPLE 7

An emulsifiable concentrate was made up by mixing the ingredients, and stirring the mixture until all the constituents were dissolved.
  Compound No. 4 of Table I: 10%
  Ethylene dichloride: 40%
  Calcium dodecylbenzenesulphate: 5%
  "Lubrol" L: 10%
  "Aromasol" H: 35%

EXAMPLE 8

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.
  Compound No. 5 of Table I: 50%
  "Dispersol" T: 25%
  "Lubrol" APN5: 1.5%
  Sodium acetate: 23.5%

EXAMPLE 9

The ingredients were all ground together to produce a powder formulation readily dispersible in liquids.
  Compound No. 4 of Table I: 45%
  "Dispersol" T: 5%
  "Lissapol" NX: 0.5%
  "Cellofas" B600: 2%
  Sodium acetate: 47.5%

EXAMPLE 10

The active ingredient was dissolved in a solvent and the resultant liquid was sprayed on to the granules of China clay. The solvent was then allowed to evaporate to produce a granular composition.
  Compound No. 5 of Table I: 5%
  China clay granules: 95%

EXAMPLE 11

A composition suitable for use as a seed dressing was prepared by mixing the three ingredients.
  Compound No. 4 of Table I: 50%
  Mineral Oil: 2%
  China clay: 48%

EXAMPLE 12

A dusting powder was prepared by mixing the active ingredient with talc.
  Compound No. 5 of Table I: 5%
  Talc: 95%

EXAMPLE 13

A Col formulation was prepared by ball-milling the constituents set out below and then forming an aqueous suspension of the ground mixture with water.
  Compound No. 4 of Table I: 40%
  "Dispersol" T: 10%
  "Lubrol" APN5 1: 1%
  Water:

EXAMPLE 14

A dispersible powder formulation was made by mixing together the ingredients set out below and then grinding the mixture until all were thoroughly mixed.
  Compound No. 5 of Table I: 25%
  "Aerosol" OT/B: 2%
  "Dispersol" AC: 5%
  China clay: 28%
  Silica: 40%

EXAMPLE 15

This Example illustrates the preparation of a dispersible powder formulation. The ingredients were mixed and the mixture then ground in a comminution mill.
  Compound No. 4 of Table I: 25%
  "Perminal" BX: 1%
  "Dispersol" T: 5%
  Polyvinylpyrrolidone: 10%
  Silica: 25%
  China clay: 34%

EXAMPLE 16

The ingredients set out below were formulated into a dispersible powder by mixing then grinding the ingredients.
  Compound No. 5 of Table I: 25%
  "Aerosol" OT/B: 2%
  "Dispersol" A: 5%
  China clay: 68%

In Examples 7 to 16 the proportions of the ingredients given are by weight.

The remaining compounds of Table I were formulated in the same way as described in Examples 7 to 16.

There now follows an explanation of the compositions or substances represented by the various Trade Marks and Trade Names mentioned above.

LUBROL L: a condensate of nonyl phenol (1 mole) with ethylene oxide (13 moles)
AROMASOL H: a solvent mixture of alkylbenzenes
DISPERSOL T & AC: a mixture of sodium sulphate and a condensate of formaldehyde with sodium naphthalene sulphonate LUBROL APN5: a condensate of nonyl phenol (1 mole) with naphthalene oxide (5.5 moles)
CELLOFAS B600: a sodium carboxymethyl cellulose thickener LISSAPOL NX: a condensate of nonyl phenol (1 mole) with ethylene oxide (8 moles)
AEROSOL OT/B: dioctyl sodium sulphosuccinate
PERMINAL BX: a sodium alkyl naphthalene sulphonate

EXAMPLE 17

The compounds were tested against a variety of mainly folia fungal diseases of plants. The techniques employed were as follows.

For all tests other than that against *Botrytis cinerea*, the plants were grown in John Innes Potting Compost (No 1 or 2) in 4cm diameter minipots. The test compounds were formulated either by bead milling with aqueous Dispersol T or as a solution in acetone or acetone/ethanol which was diluted to the required concentration immediately before use. For the foliage diseases, solutions and suspensions (100ppm ai) were sprayed on the foliage and applied to the roots of the plant via the soil. For the test against *Botrytis cinerea*, grape berries were sprayed with the test compounds. The sprays were applied to maximum retention and the root drenches to a final concentration equivalent to approximately 40ppm ai/dry soil. Tween 20, to give a final concentration of 0.05%, was added when the sprays were applied to cereals (ai means "active ingredient").

Most were protectant tests where the compound was applied to the soil and roots and to the foliage one or two days before the plant was inoculated with the pathogen. However, in the case of the tests against *Erysiphe graminis hordei* and *Botrytis cinerea*, the treatment was eradicative and the compounds were applied one day after inoculation.

Inoculation of the grape berries in the *Botrytis cinerea* test was acheived by slitting fruits twice and then immersing them in a spore suspension of the pathogen. The remaining foliar pathogens were applied by spray as spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:
4 = no disease
3 = trace to 5% of disease on untreated plants
2 = 6–25% of disease on untreated plants
1 = 26–59% of disease on untreated plants
0 = 60–100% of disease on untreated plants
The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | BOTRYTIS CINEREA (GRAPE) | CERCOSPORA ARACHIDICOLA (PEANUT) | VENTURIA INAEQUALIS (APPLE) |
| --- | --- | --- | --- | --- | --- | --- | --- |
| 1   | 3 | 4 | — | 0 | 0 | 4 | 4 |
| 2   |   |   |   |   |   |   |   |
| 3   | 4 | 4 | 2 | 0 | 0 | 4 | 4 |
| 4   | 4 | 4 | — | 1 | 0 | 4 | 4 |
| 5   | 4 | 4 | — | 0 | 0 | 4 | 4 |
| 6*  | 0 | 3 | 0 | 0 | 0 | 4 | 4 |
| 7   | 2 | 4 | 2 | 4 | 0 | 2 | 0 |
| 8*  | 0 | 4 | 0 | 0 | 0 | 1 | 3 |
| 9   | 4 | 4 | 0 | 0 | 0 | 0 | 2 |
| 10  | 3 | 4 | 4 | 0 | 0 | 4 | 4 |
| 11  |   |   |   |   |   |   |   |
| 12  | 0 | 4 | 1 | 0 | 0 | 3 | 4 |
| 14  | 0 | 4 | 0 | 0 | 0 | 3 | 3 |
| 15  |   |   |   |   |   |   |   |
| 16  | 0 | 4 | 0 | 0 | 0 | 2 | 1 |
| 17  | 0 | 2 | 3 | 3 | 0 | 1 | 3 |
| 18  | 0 | 1 | 1 | 0 | 0 | 0 | 4 |
| 19  | 4 | 4 | 3 | 0 | 0 | 3 | 4 |
| 20  | 0 | 3 | — | 0 | 0 | 0 | 0 |
| 21  | 0 | 3 | 0 | 0 | 0 | 1 | 1 |
| 22  | 0 | 4 | 0 | 0 | 0 | 3 | 3 |
| 23  | 4 | 4 | — | 0 | 0 | 4 | 4 |
| 24  | 0 | 4 | 3 | 0 | 0 | 3 | 4 |
| 25  | 4 | 4 | 3 | 1 | 0 | 4 | 4 |
| 26  | — | — | — | — | — | — | — |
| 27  | — | — | — | — | — | — | — |
| 28* | 0 | 4 | 0 | 0 | — | 0 | 4 |
| 29  | 0 | 4 | 0 | 0 | — | 2 | 0 |
| 30  | — | 4 | 3 | 0 | — | 4 | 4 |
| 31  | — | — | — | — | — | — | — |
| 32  | — | — | — | — | — | — | — |
| 33  | — | — | — | — | — | — | — |
| 34  | — | — | — | — | — | — | — |
| 35  | — | — | — | — | — | — | — |
| 36  | 4 | 4 | 3 | 0 | — | 4 | 4 |
| 37  | 4 | 4 | 1 | 0 | — | — | 4 |
| 38  | — | — | — | — | — | — | — |
| 39  | — | — | — | — | — | — | — |
| 40  | — | — | — | — | — | — | — |

*Protectant test at 25 ppm
"—" means not tested

EXAMPLE 18

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Plant growth regulating effects were assessed 13 or 19 days after application of the compounds. Retardation of growth was scored on a 1-3 scale where:

1 = 0-30% retardation
2 = 31-75% retardation
3 = 75% retardation or more

The absence of any numeral 1 to 3 signifies no effect. Additional plant growth regulating properties are indicated as follows:

G = darker green leaf colour
A = apical effect
T = tillering effect

The results are shown in Table III. If no figure is shown the compound was substantially inactive as a stunting agent.

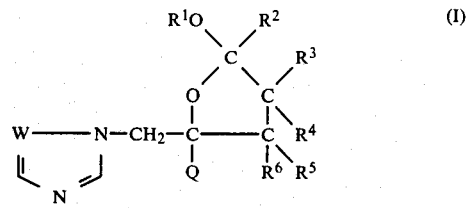

and stereoisomers thereof, wherein W is CH or N; Q is $C_{1-6}$ alkyl, phenyl or benzyl, or phenyl or benzyl substituted with halogen, $C_{1-6}$ haloalkyl, $C_{1-6}$ alkyl, $C_{1-6}$ alkoxy, phenyl, benzyl or phenoxy, $R^1$ is H, $C_{1-6}$ alkyl, $C_{3-6}$ cycloalkyl, $C_{2-6}$ alkenyl, $C_{2-6}$ alkynyl, alkylcarbonyl having one to seven carbon atoms in the alkyl moiety, $C_{1-4}$ alkoxycarbonyl, $C_{1-4}$ alkoxyalkyl, ethoxycarbonylmethyl, 1-propenyloxymethyl, 2,4-dichlorobenzyloxyethyl, 4-nitrophenylcarbonyl, $C_{1-6}$ hydroxyalkyl, phenyl or benzyl, or phenyl or benzyl substituted with halogen, $C_{1-6}$ haloalkyl, $C_{1-6}$ alkyl, $C_{1-6}$ alkoxy, phenyl, benzyl or phenoxy; $R^2$, $R^3$, $R^4$, $R^5$ and $R^6$, which may be the same or different, H, $C_{1-6}$ alkyl or $C_{3-6}$ cycloalkyl,

| COMPOUND NO. | DAT | RATE | SY | RA | SB | VN | AT | CC | DA | WW | BR | MZ | LT | TO | CT |
|---|---|---|---|---|---|---|---|---|---|---|---|---|---|---|---|
| 1 | 15 | 4000 | 2G | | 1G | | | | | | | 2 | | 1G | 1 |
| 2 | 19 | 4000 | 1GA | 2 | 3G | 2T | 2 | 2 | 2 | 1T | 1T | 3A | 1 | 3A | |
| 3 | 19 | 4000 | G | | 3G | 3 | 2 | 2 | 2 | 2T | 1 | 1 | 3 | 3A | |
| 4 | 15 | 4000 | 2GA | 3G | 3G | | 1G | 1G | 1G | 2GT | 2GT | 3G | 2G | 2G | 2G |
| 5 | 15 | 4000 | 2G | 3G | 3G | | 1G | 1G | 1G | 3GT | 2GT | 3G | 3G | 2G | 3GA |
| 7 | 18 | 4000 | 1G | | 2G | | 3G | 2 | 1 | 2G | 1 | | 1 | 2 | |
| 9 | 18 | 2000 | 1G | | 1 | 2 | | | | 1 | 1 | | | 2T | 1A |
| 12 | 18 | 4000 | 1 | | 2G | | | | | 1G | 1 | | | 2GT | 1 |
| 14 | 18 | 4000 | 1 | | 2G | | 1 | 1 | 1 | 1G | | | | 1T | |
| 15 | 18 | 4000 | | | 1 | | | | | 1 | | | | | |
| 17 | 18 | 4000 | 2G | | | 1 | | | | 3GT | 1 | | | 2T | 1 |
| 18 | 18 | 2000 | | | | 3A | | | | 1 | 1 | | | T | |
| 19 | 15 | 4000 | 2 | | 1G | | 1 | 1 | 1 | | | | | 1GT | |
| 20 | 15 | 4000 | 1 | | 2G | | | | | | | | | 1G | |
| 21 | 18 | 2000 | 1T | | | | | | | 1T | 1 | | | 1 | |
| 23 | 15 | 4000 | | | 1 | 3G | 3G | 3G | | | | | | | |
| 24 | 18 | 4000 | 1GT | | 1 | 3A | | | | | | | | 2AT 3GA | |
| 25 | 12 | 3000 | G | 2G | G | | 1 | 1 | 1 | 1 | 1 | 1 | 1 | 1G | |
| 26 | 13 | 4000 | 1 | | 3GA | 3A | 1 | 1 | 1 | T | T | 3 | 1G | 3GA | |
| 27 | 13 | 4000 | | | 1G | 1T | | | | T | | | 2A | 2AT | |
| 28 | 12 | 4000 | G | | 3G | 3A | 1 | 1 | | T | | | 2G | 3GAT | |
| 29 | 12 | 4000 | | | 1 | 1 | | | | T | | | | 1 | |
| 30 | 12 | 4000 | 1G | | 2GA | 2 | 2 | 1 | | T | T | 1 | 1 | 1G | |
| 31 | 12 | 4000 | GT | | 2GA | 2T | 2 | 2 | 1 | T | T | | 2G | 2GA | |
| 32 | 12 | 4000 | G | | 2GA | 1 | 2G | 2G | G | GT | GT | 1G | 3GA | 3GA | |
| 33 | 12 | 4000 | G | | 2G | | | | | T | T | | 1G | 1G | |
| 35 | 19 | 4000 | 1G | | 2GA | 2T | 1G | 1G | 1G | 1T | | 2 | 1 | 2GAT | |
| 36 | 19 | 4000 | T | | 2G | 3AT | 1G | 2G | G | | | | 1 | 3AT | |
| 37 | 12 | 4000 | 1 | | 2GA | 1T | 1 | 1 | 1 | T | T | | 2G | 1GT | |
| 38 | 12 | 4000 | 1 | | 1G | 2GA | | 1 | | 1 | | | 3GA | 3A | |
| 39 | 12 | 4000 | 1G | | 2GA | 2GA | 2T | 3 | 2 | 1 | T | T | 1G | 2G | 3GAT |
| 40 | 12 | 4000 | | | 1G | 3T | 1 | 1 | 1 | 3GT | 3GT | | 2G | 2G | |

Key to test species in Table III
SY Glycine max
CT Gossypium hirsutum
SB Beta vulgaris
AT Agrostis tenuis
CC Cynosurus cristatus
DA Dactylis glomerata
WW Triticum aestivum
BR Hordeum vulgare
MZ Zea mays
LT Lactuca sativa
TO Lycopersicon esculentum
VN Vitus vinifera
RA Raphanus raphinistrum

We claim:
1. A compound having the formula (I):

phenyl or benzyl; and acid salts and metal complexes thereof.

2. A compound according to claim 1 having the formula (I):

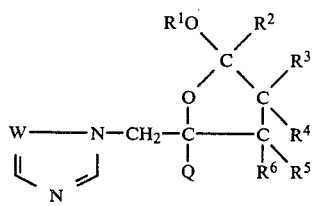

and stereoisomers thereof, wherein W is N; Q is halo-substituted phenyl; $R^1$ is H, $C_{1-6}$ alkyl, $C_{3-6}$ cycloalkyl, propargyl, alkylcarbonyl having one to seven carbon atoms in the alkyl moiety, $C_{1-4}$ alkoxycarbonyl, phenyl or phenyl substituted with halogen, $C_{1-6}$ haloalkyl, $C_{1-6}$ alkyl, $C_{1-6}$ alkoxy, phenyl, benzyl, or phenoxy; benzyl or benzyl substituted with halogen, $C_{1-6}$ haloalkyl, $C_{1-6}$ alkyl, $C_{1-6}$ alkoxy, phenyl, benzyl, or phenoxy, or $C_{1-4}$ hydroxyalkyl; $R^2$ is H or $C_{1-4}$ alkyl, $R^3$, $R^4$, $R^5$ and $R^6$ are H; and acid salts and metal complexes thereof.

3. A compound as defined in claim 1 wherein Q or $R^1$ is selected from the group consisting of 2-, 3- or 4-chlorophenyl, 2,4- or 2,6-dichlorophenyl, 2,4- or 2,6-difluorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxyphenyl, 2-fluoro-4-chlorophenyl, 2-chloro-4-fluorophenyl, 2-, 3- or 4-methylphenyl, 2-, 3- or 4-ethylphenyl, 2-, 3- or 4-trifluoromethylphenyl, 4-phenylphenyl, 2-chloro-4-methoxyphenyl, 2-chloro-4-methylphenyl, 2-fluoro-4-methylphenyl, 4-isopropylphenyl, 2-methyl-4-chlorophenyl or 2-methyl-4-fluorophenyl.

4. A compound as defined in claim 1 wherein $R^1$ and/or $R^2$ is selected from the group consisting of ethyl, propyl, butyl, cyclopropyl, cyclobutyl, cyclopentyl or cyclohexyl.

5. A fungicidal, or plant growth regulating composition comprising an effective amount of a compound of general formula (I) as defined in claim 1 or a salt or complex thereof, and a carrier or diluent.

6. A method of regulating the growth of plants, which comprises applying to the plant, to seed of the plant, or to the locus of the plant or seed, an effective amount of a compound or a salt or complex thereof, as defined in claim 1.

7. A method of combating fungal diseases in a plant, which method comprises applying to the plant, to seed of the plant or to the locus of the plant or seed, an effective amount of a compound, or a salt or complex thereof, as defined in claim 1.

* * * * *